United States Patent [19]

Sano et al.

[11] 4,359,374
[45] Nov. 16, 1982

[54] OXYGEN SENSOR

[75] Inventors: Hiromi Sano, Nagoya; Masatosi Suzuki; Masaya Fujimoto, both of Kariya, all of Japan

[73] Assignees: Nippondenso Co., Ltd., Kariya; Toyota Jidosha Kogyo Kabushiki Kaisha, Toyota, both of Japan

[21] Appl. No.: 231,318

[22] Filed: Feb. 4, 1981

Related U.S. Application Data

[63] Continuation of Ser. No. 92,038, Nov. 7, 1979, abandoned, which is a continuation of Ser. No. 889,503, Mar. 23, 1978, abandoned.

[51] Int. Cl.$^3$ ............................................. G01N 27/58
[52] U.S. Cl. ................................................. 204/195 S
[58] Field of Search .............. 204/195 S, 15; 123/489; 60/276

[56] References Cited

U.S. PATENT DOCUMENTS

| | | | |
|---|---|---|---|
| 2,872,312 | 2/1959 | Eisenberg | 75/212 |
| 3,468,780 | 9/1969 | Fischer | 204/195 S |
| 3,843,400 | 10/1974 | Radford et al. | 204/195 S X |
| 3,978,006 | 8/1976 | Topp et al. | 204/195 S X |
| 4,021,326 | 5/1977 | Pollner et al. | 204/195 S |
| 4,107,018 | 8/1978 | Bode et al. | 204/195 S |
| 4,135,012 | 1/1979 | Su | 427/309 |

OTHER PUBLICATIONS

The Merck Index, p. 631, (1976).

*Primary Examiner*—G. L. Kaplan
*Attorney, Agent, or Firm*—Cushman, Darby & Cushman

[57] ABSTRACT

An oxygen sensor for detecting an oxygen concentration in a gas under test such as exhaust gas from an internal combustion engine of an automobile. The oxygen sensor comprises an oxygen concentration sensing element made of an oxygen ion conductive metal oxide which produces an electromotive force in accordance with a difference between an oxygen concentration in the gas under test and an oxygen concentration in a reference gas, a porous layer of refractory metal oxide formed on a surface of the oxygen concentration sensing element which is to be exposed to the gas under test, and an electrode formed thereon. The peel-off of the electrode is prevented and a high-response oxygen sensor is provided.

11 Claims, 5 Drawing Figures

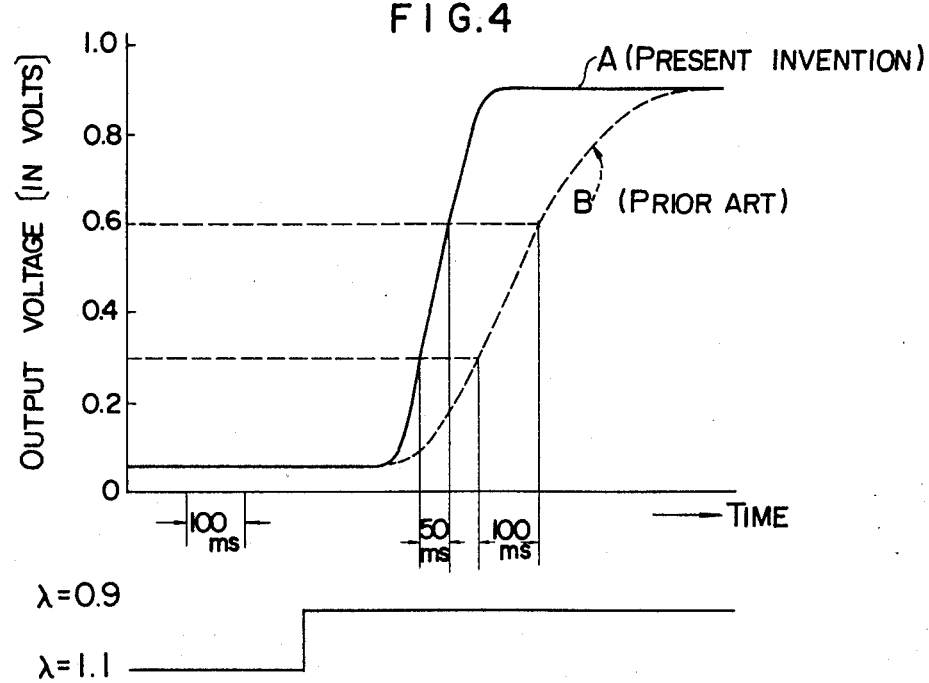
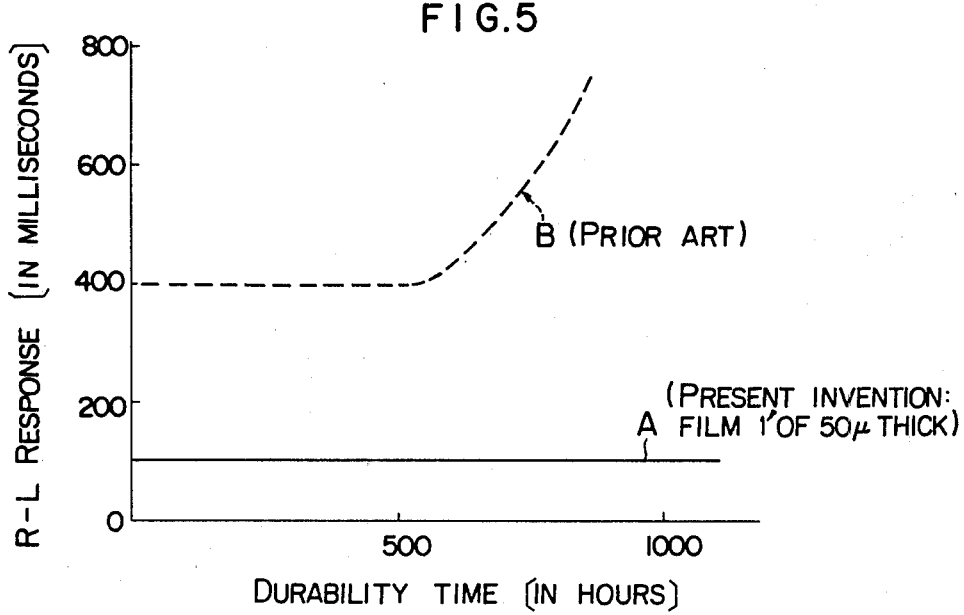

OXYGEN SENSOR

This is a continuation, of application Ser. No. 92,038 filed Nov. 7, 1979, now abandoned; which is a continuation of Ser. No. 889,503 filed Mar. 23, 1978, now abandoned.

BACKGROUND OF THE INVENTION

The present invention relates to an oxygen sensor for sensing an oxygen concentration in gas components of a gas under test such as exhaust gas from an internal combustion engine of an automobile, and more particularly to a high-response oxygen sensor which can prevent the peel-off of an electrode on the side of the sensor which is to be exposed to the gas under test.

A prior art oxygen sensor includes an oxygen concentration sensing element made of an oxygen ion conductive metal oxide such as $ZrO_z$-CaO, and thin film platinum (Pt) electrodes are formed on the surfaces of the oxygen concentration sensing element which are to be exposed to a reference gas and the gas under test, respectively, by chemical plating, vapor deposition or the like.

In the prior art sensor, the oxygen concentration sensing element is highly sintered to form a fine structure because an electromotive force will not be produced if the gas transmits through the oxygen concentration sensing element as the oxygen concentration sensing element is to sense a differential oxygen concentration between the gas under test and the reference gas. As the oxygen concentration sensing element is highly sintered, the adhesion of the electrodes to the sensing element is so weak that when they are left exposed to the gas under test for a long time they are peeled off from the surface of the oxygen concentration sensing element. A difference between thermal expansions of the electrodes and the sensing element also contributes to the peel-off of the electrode.

In order to resolve the above problem, it has been proposed to sand-blast the surface of the oxygen concentration sensing element, which is exposed to the gas under test, to make the surface rough and form fine projections and recesses (namely, to give surface porosity) in order to enhance the adhesion of the electrode and improve the anti-peel-off property of the electrode. However, although the sand-blasted oxygen concentration sensing element has an improved anti-peel-off property, fine cracks are formed on the surface of the oxygen concentration sensor so that the mechanical strength thereof is lowered and the oxygen concentration sensor may be destroyed when it is used in a vibrating environment for a long time. Thus, it has a problem of low durability.

In order to improve the response and the precision of the oxygen concentration sensing element, it has been proposed, as disclosed in U.S. Pat. No. 3,935,089 to form a porous inorganic material on an outer surface of the electrode to carry thereon a catalytic material to promote equilibrium of oxygen partial pressure so that an electromotive force changes abruptly near a stoichiometric air-fuel ratio. Since this type of oxygen sensor is not practical without the catalytic material carried on the outer surface of the electrode, the cost of the sensor is increased when a noble metal such as platinum is used as the catalytic material.

It is an object of the present invention to provide an oxygen sensor having an oxygen concentration sensing element in which a porous film made of a refractory metal oxide is formed on a surface of the oxygen concentration sensing element which is to be exposed to a gas under test and an electrode is formed on the porous film.

DETAILED DESCRIPTION OF THE INVENTION

It is another object of the present invention to provide an oxygen sensor which prevents the peel-off of the electrode, has a high response and is inexpensive.

The oxygen concentration sensing element and the porous film used in the oxygen sensor of the present invention are both metal oxides and hence adaptable to each other, so that the film strongly adheres to the surface of the oxygen concentration sensing element. Furthermore, since the film is porous and hence has a large surface area, the electrode strongly adheres to the film. Therefore, the adhesion of the electrode to the oxygen concentration sensing element can be enhanced without surface treatment such as sand blasting. As a result, the problem of the destruction of the oxygen concentration sensing element due to the sand blasting is avoided and a high durability oxygen sensor can be provided.

In the present invention, while any refractory metal oxide may be used as a material for the porous film, a material of the same composition as the oxygen concentration sensing element or of similar composition to the latter is preferable. When the porous film has such a composition, the oxygen ion conduction is not impeded and a stable characteristic of the oxygen concentration sensing element is obtained. It should be understood, however, that in attaining the object of the present invention of enhancing the adhesion of the electrode any refractory metal oxide may be used.

BRIEF DESCRIPTION OF THE DRAWINGS

These and other objects, features and advantages of the present invention will be apparent from the following detailed description of the preferred embodiment of the invention, when taken is conjunction with the accompanying drawings, in which;

FIGS. 3 and 4 show response characteristics of the oxygen sensor in accordance with the embodiment of the present invention and a prior art oxygen sensor; and FIG. 5 shows responses to durability time of the oxygen sensor in accordance with the embodiment of the present invention and the prior art oxygen sensor.

DETAILED DESCRIPTION OF THE DRAWINGS

Figure 1:
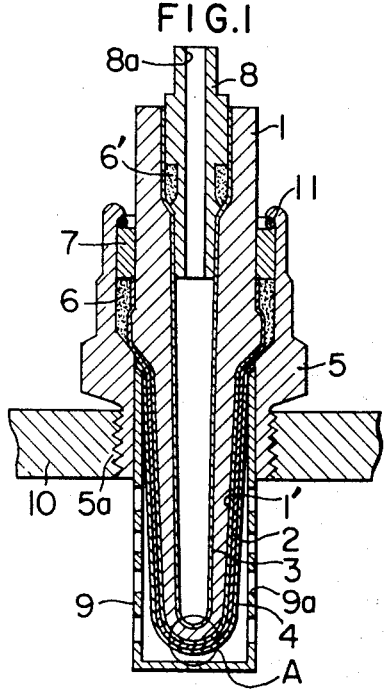
FIG. 1 is a sectional view illustrating one embodiment of an oxygen sensor of the present invention.
Figure 2:
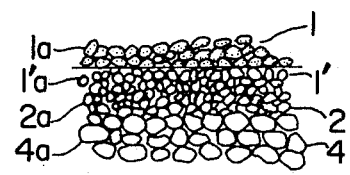
FIG. 2 is a system diagram showing a section A in FIG. 1 in an enlarged scale.

Referring to FIG. 1, numeral 1 denotes an oxygen concentration sensing element made of an oxygen ion conductive metal oxide, which is a finely sintered body of 70-95 mole % of metal oxide such as $ZrO_2$, $ThO_2$ or $CeO_2$ to which 30-5 mole % of divalent or trivalent metal oxide was dissolved by solid solution. In the illustrated embodiment, 90 mole % of $ZrO_2$ and 10 mole % of $Y_2O_3$ are mixed, and the mixture is ground and calcined and formed into a desired cup-shape, which is then fired at approximately 1600°–1750° C. to form a finely sintered body. A porous film 1' is formed on an outer circumference of the oxygen concentration sensing element 1. It is formed by grinding the calcined mixture of 90 mole % of $ZrO_2$ and 10 mole % of $Y_2O_3$ (grain size of 1–20μ), adding small amount of water to make the mixture muddy, spraying the muddy mixture on the outer circumference of the oxygen concentration sensor 1 or painting it to the thickness of 20–200μ and firing the oxygen concentration sensor 1 at 1600°–1750° C. Numeral 2 denotes a porous layer of a first electrode which is formed on a surface of the film 1' by depositing thereon platinum having a catalytic action by chemical plating, vapor deposition or paste application, and numeral 3 denotes a second electrode formed by depositing platimum having a catalytic action on an inner circumference of the oxygen concentration sensing element 1 by chemical plating or paste application. A porous coating 4 of the thickness of 50–100μ is formed on the surfaces of the first electrode 2 in order to protect the first electrode 2 from the exhaust gas and stabilize an output of the detector. The coating 4 may comprise an oxide or composite oxide such as $Al_2O_3$, $Al_2O_3$-$SiO_2$, $MgO$-$Al_2O_3$ or $ZrO_2$. Numeral 5 denotes a housing which is used to directly screw the detector to an exhaust pipe 10 and has a threaded portion 5a at the bottom thereof. The oxygen concentration sensing element 1 and the housing 5 are secured to each other by pressing an O-ring 7 with a conductive metal material 6 which is interposed therebetween. Numeral 8 denotes a metal stem pressed into the bore of the sensing element 1 with a conductive material 6' interposed between the oxygen concentration sensing element 1 and the stem 8. The stem 8 is formed with a bore 8a through which the inner circumference of the oxygen concentration sensing element 1 is exposed to the atmosphere as a reference gas. The housing 5 is electrically connected to the first electrode 2 through the conductive material 6 so that the housing 5 constitutes one of the electrodes from which an output is taken, while the stem 8 is electrically connected to the second electrode 3 through the conductive material 6' so that the stem 8 constitutes the other electrode. Numeral 9 denotes a protective metal tube having a number of pores 9a, which is provided to relax the direct contact of the outer circumference of the oxygen concentration sensing element 1 to the exhaust gas. Numeral 11 denotes a conductive ring. In FIG. 2, numeral 1a denotes component grains of the oxygen concentration sensing element 1 and numeral 1a' denotes component grains of the film 1'. Numeral 2a denotes component grains of the electrode 2 and numeral 4a denotes component grains of the coating 4.

The operation of the structure described above is now explained. The oxygen sensor is mounted on the exhaust pipe 10 by the housing 5 so that the oxygen concentration sensing element 1 is exposed to the exhaust gas. As is well known, the exhaust gas comprises component gases such as $O_2$, CO and HC, and the concentrations of those component gases change with an air-fuel ratio before combustion of the air-fuel mixture. The oxygen concentration sensing element 1 produces an electromotive force in accordance with a difference between an oxygen concentration in the exhaust gas and an oxygen concentration in the atmosphere which acts as a reference gas. The electromotive force is high (0.9 V) on the rich side of the air-fuel ratio and low (0.1 V) on the lean side of the air-fuel ratio, and abruptly changes at a stoichiometric air-fuel ratio. $N.O_x$ component is less on the rich side of the air-fuel ratio while HC and CO components are less on the lean side of the air-fuel ratio, and it is near the stoichiometric ratio that the amount of those three components is minimum. Accordingly by managing the electromotive force of the detector at the stoichiometric air-fuel ratio to control the air-fuel ratio of the air-fuel mixture, the exhaust gas can be purified in a very efficient way.

In the present embodiment, since the film 1' formed on the surface of the oxygen concentration sensing element 1 has the same composition as the oxygen concentration sensing element and thereby thermal expansions thereof are equal to each other, they are adaptable to each other and the adhesion of the film 1' to the oxygen concentration sensing element 1 is very strong. Accordingly, the film 1' is not peeled off and the oxygen ion conductivity is not affected. Since the film 1' is porous, the contact area of the electrode 2 to the film 1' increases and the component grains of the electrode 2 deeply penetrate into the film 1'. Accordingly, the adhesion of the electrode 2 to the film 1' is very strong and the electrode 2 is not peeled off from the film 1' even after the long term usage, and hence the electrode 2 is not peeled off from the oxygen concentration sensing element 1.

Figure 3:
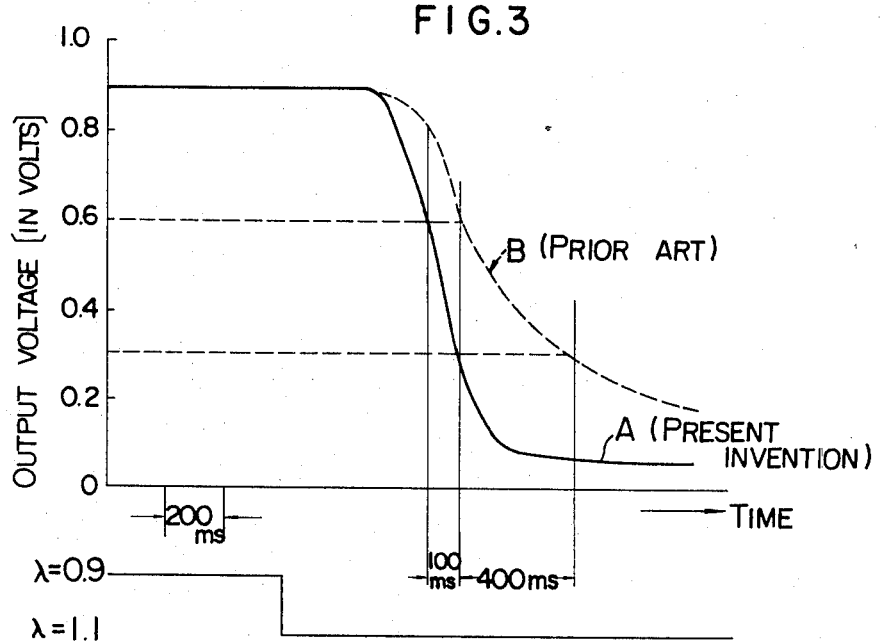

Furthermore, when the electrode 2 is made of a metal having a catalytic action such as platinum, since the platinum electrode is carried by the porous film 1' to provide a large catalytic active area, it is not always necessary to carry another metal having a catalytic action on the outer surface of the electrode 2. The inventors of the present invention have found the following from an experiment. FIGS. 3 and 4 show the comparative responses of the sensor of the present invention (Sample A: with the film 1' of the thickness of 50μ) and a prior art sensor (Sample B: with an electrode directly formed on the surface of the sensing element). FIGS. 3 and 4 show the response times of the samples A and B in an engine having six cylinders and a capacity of 2,000 cc, at a revolution speed of 2,000 rpm and at an exhaust gas temperature of 450° C. FIG. 3 shows the response times measured when an air excessive factor λ of air-fuel mixture to be fed to the engine was changed from 0.9 to 1.1 (air-fuel ratio: rich to lean) so that an output voltage of the sensor changed from 0.6 V to 0.3 V, and FIG. 4 shows the response time measured when the air excessive factor was changed from 1.1 to 0.9 (air-fuel ratio: lean to rich) so that the output voltage of the sensor changed from 0.3 V to 0.6 V. In FIGS. 3 and 4, the solid lines show the output voltage characteristics of the sensor of the present invention (Sample A) and the broken lines show the output voltage characteristics of the prior art sensor (Sample B). It is apparent from the above experiment that the response of the sensor of the present invention is much superior to that of the prior art sensor.

Another experiment was carried out to determine the durability and the anti-peel-off property of the sensor of the present invention. The sensor of the present invention shown in FIG. 1 (Sample A: with the film 1' having the thickness of 50μ) and the prior art sensor (Sample B) were placed in an electric oven at 1,000° C. for 20 minutes, and they were then cooled to a room temperature and then again placed in the electric oven at 1,000° C. for 20 minutes. The above cycle was repeated 200 times. In the sensor shown in FIG. 1, the electrode 2 was not peeled off at all, while in the prior art sensor in which the electrode was formed directly on the surface of the oxygen concentration sensing element, the electrode was partially peeled off. Further, a bending strength was measured for the oxygen concentration sensing element having the surface sand blasted in a conventional manner. The result was that the bending strength thereof was lower than that of the oxygen concentration sensing element of the present embodiment having the surface not sand blasted, by approximately 50%.

A further experiment was carried out to determine the durability and the response of the sensor of the present invention. The sensor of the present invention (Sample A) and the prior art sensor (Sample B) were tested for the durability under the following operation conditions and the response times of the Samples A and B under the respective durability times when λ was changed from 0.9 to 1.1 were measured. The results are shown in FIG. 5.

Operation conditions:
engine; 2,000 cc, six cylinders.
exhaust gas temperature; 850° C.
air-fuel ratio; 14.

It is seen from FIG. 5 that in the Sample B the response time becomes longer (deterioration is meant) when the durability test is continued over 500 hours, while in the Sample A the response time does not substantially change even after 1,000 hour durability test.

Furthermore, in the present embodiment, since the porous coating 4 is formed on the surface of the electrode 2, lead, oil and phosphorus in the exhaust gas deposit on the coating 4 but do not deposit directly on the electrode 2, and hence the catalytic action of the electrode 2 is not deteriorated. In essence, the coating 4 functions as a filter.

The present invention is not limited to the illustrated embodiment but various modifications as shown below may be made:

(1) The firing process of the material of the film 1' may be omitted by depositing the material of the film 1' on the surface of the cup-shaped mold which is to form the oxygen concentration sensing element 1 before the mold is fired and then firing the mold.

(2) Although the material of the film 1' is the same as the material of the oxygen concentration sensing element 1 (solid solution composition of $ZrO_2$ and $Y_2O_3$), it may be an oxygen ion conductive metal oxide other than $ZrO_2$-$Y_2O_3$, such as $ZrO_2$-CaO or $ZrO_2$-MgO, or even a metal oxide other than the oxygen ion conductive metal oxide, such as $Al_2O_3$ or MgO-$Al_2O_3$.

(3) The material of the film 1' may be deposited on the surface of the oxygen concentration sensing element 1 by plasma injection-welding and then firing the sensing element at 1,400°–1,600° C. in order to further enhance the adhesion between the oxygen concentration sensing element 1 and the film 1'.

(4) The surface of the film 1' may be chemically etched by strong acid such as hydrofluoric acid before the electrode 2 is deposited on the surface of the film 1' in order to further enhance the adhesion between the film 1' and the electrode 2.

Thus when film 1' is chemically etched with a strong acid, for example, the etching liquid penetrates into the porous film 1' to corrode the particle surfaces of the metal oxide forming film 1' and form fine apertures therein. This porosity allows the metal particles of the electrode 2 to enter into a portion of film 1' to establish a strong adhesion between the film 1' and the electrode 2.

(5) While the conductive material of the electrodes 2 and 3 is platinum in the illustrated embodiment, it may be other material having a catalytic action such as Pd, Rh, Au, Ru or Ag, or an alloy thereof, or different metals may be used for the electrodes 2 and 3, such as Pd for the electrode 2, Pt for the electrode 3 and Pd for the thick film.

(6) While the oxygen concentration sensing element 1 is of cup-shape having one end opened and the other end closed in the illustrated embodiment, it may be of plate shape or cylinder shape.

Furthermore, the present invention is not limited to means for sensing the oxygen concentration in the exhaust gas from the internal combustion engine to detect the air-fuel ratio of the air-fuel mixture to be fed to the internal combustion engine as shown in the illustrated embodiment, but the present invention may be used as means for sensing an oxygen concentration in a combustion product exhausted from a combustion mechanism such as a blast furnace or boiler to detect an air-fuel ratio of air-fuel mixture to be supplied to the combustion mechanism (for example, for improving a thermal efficiency of the combustion mechanism).

An experiment by the inventors has proved that when the oxygen concentration sensing element 1 was made of an oxygen ion conductive metal oxide consisting of 90–92 mole % of $ZrO_2$ and 10–8 mole % of $Y_2O_3$, the conductivity is so increased that the conduction of the oxygen ion was carried out even at a low temperature.

As described hereinabove, according to the present invention, since the film of the refractory porous metal oxide is formed on the surface of the oxygen concentration sensing element which is to be exposed to the gas under test and the electrode is formed on the surface of the film, both the oxygen concentration sensing element and the film are made of the metal oxide and they are compatible with each other. Accordingly, the film is strongly adhered to the oxygen concentration sensing element. Further, since the film is porous, it has a large contact area with the electrode and a portion of the electrode penetrates into the pores of the film. Therefore, the electrode is strongly adhered to the film and the adhesion of the oxygen concentration sensing element to the electrode is very strong without requiring the sand blasting process. Accordingly, the problem of decrease of the strength of the oxygen concentration sensing element due to sand blasting, which was encountered in the prior art sensor, is not raised.

We claim:

1. An oxygen sensor for detecting an oxygen concentration in an exhaust gas from an internal combustion engine of an automobile, said sensor comprising:
a solid oxygen concentration sensing element made of an oxygen ion conductive metal oxide mixture selected from a group consisting of $ZrO_2$-$Y_2O_3$, $CrO_2$-CaO and $ZrO_2$-MgO, which produces an electromotive force in accordance with a difference between an oxygen concentration in the exhaust gas and an oxygen concentration in a reference gas;
a first porous film made of a refractory metal oxide formed on a surface of said oxygen concentration sensing element which is to be exposed to the exhaust gas said refractory metal oxide being an oxygen ion conducting metal oxide mixture and selected from the group consisting of $ZrO_2$-$Y_2O_3$, $ZrO_2$-CaO and $ZrO_2$-MgO, said first porous film having a porous, chemically etched surface upon which a first electrode is formed;
a first electrode formed on said first porous film such that component grains of said first electrode penetrate into said first porous film, said first electrode being catalytically active;

a second porous film formed on said first electrode for protecting said first electrode from the exhaust gas; and a second electrode formed on the opposite surface of said oxygen concentration sensing element.

2. An oxygen sensor according to claim 1 wherein said oxygen concentration sensing element and said first porous film have the same composition.

3. An oxygen sensor according to claim 1, wherein said first electrode is made of a catalytically active metal selected from the group consisting of Pt, Rh, Au, Ru and Ag or an alloy thereof.

4. An oxygen sensor according to claim 1 wherein said oxygen concentration sensing element consists of 90–92 mole % of $ZrO_2$ and 10–8 mole % of $Y_2O_3$.

5. An oxygen sensor according to claim 1, wherein said second porous film is made of a material selected from a group consisting of an oxide of $Al_2O_3$, an oxide of ZrO a composite oxide of $Al_2O_3$-$SiO_2$ and a composite oxide of MgO-$Al_2O_3$.

6. An oxygen sensor according to claim 1 having a response time of about 100 milliseconds when the air-fuel mixture supplied to said engine changes from rich to lean from 0.9 to 1.1 and the output voltage of said sensor changes from 0.6 volts to 0.3 volts.

7. An oxygen sensor according to claim 1 or 6 having a response time of about 50 milliseconds when the air-fuel mixture supplied to said engine changes from lean to rich from 1.1 to 0.9 and the output voltage of said sensor changes from 0.3 volts to 0.6 volts.

8. In an oxygen sensor for detecting an oxygen concentration in an exhaust gas from an internal combustion engine of an automobile, comprising:

a solid oxygen concentration sensing element made of an oxygen ion conductive meta oxide which produces an electromotive force in accordance with a difference between an oxygen concentration in the exhaust gas and an oxygen concentration in a reference gas;

an electrode formed on a surface of said oxygen concentration sensing element; and a first porous film formed on said electrode for protecting said electrode from the exhaust gas;

the improvement wherein;

said oxygen ion conductive metal oxide is a metal oxide mixture selected from a group consisting of $ZrO_2$-$Y_2O_3$, $ZrO_2$-CaO and $ZrO_2$-MgO; and said oxygen sensor comprises:

a second porous film made of a refractory metal oxide formed directly on a surface of said oxygen concentration sensing element which is to be exposed to the exhaust gas and intermediate said electrode, said refractory metal oxide capable of conducting oxygen ions and selected from the group consisting of $ZrO_2$-$Y_2O_3$, $ZrO_2$-CaO and $ZrO_2$-MgO, said second porous film having a porous, chemically etched surface upon which said electrode is formed;

said electrode being adapted to form a porous layer of catalytically active metal and being formed on said second porous film in a condition such that component grains of said electrode penetrate into said second porous film.

9. An oxygen sensor according to claim 8 wherein said oxygen concentration sensing element and said second porous film are both refractory metal oxides of the same composition.

10. An oxygen sensor for detecting an oxygen concentration in an exhaust gas from an internal combustion engine of an automobile, comprising:

a solid oxygen concentration sensing element composed of an oxygen ion conductive oxide mixture selected from the group consisting of $ZrO_2$-$Y_2O_3$, $ZrO_2$-CaO and $ZrO_2$-MgO, which produces an electromotive force in accordance with the difference between an oxygen concentration in the exhaust gas and an oxygen concentration in a reference gas;

a first porous film that conducts oxygen ions and consists of the same metal oxide mixture as said sensing element, formed on a surface of said sensing element which is to be exposed to the exhaust gas, said first porous film having a porous, chemically etched surface which allows the metal particles of an electrode layer to be strongly adhered thereto and upon which said first electrode is formed;

a first electrode of a porous layer of metal having a catalytic action, said first electrode being formed on said first porous film in a condition that component grains of said first electrode penetrate into the porous surface of said first porous film;

a second porous film formed on said first electrode for protecting said first electrode from the gas under test; and a second electrode formed on an opposite surface of said oxygen concentration sensing element.

11. An oxygen sensor for detecting an oxygen concentration in an exhaust gas from an internal combustion engine of an automobile, comprising:

a solid oxygen concentration sensing element composed of an oxygen ion conductive metal oxide mixture selected from the group consisting of $ZrO_2$-$Y_2O_3$, $ZrO_2$-CaO and $ZrO_2$-MgO, which produces an electromotive force in accordance with the difference between an oxygen concentration in the exhaust gas and an oxygen concentration in a reference gas;

a first porous film that conducts oxygen ions and consists of the same oxide mixture as said sensing element, formed on a surface of said sensing element which is to be exposed to the exhaust gas, said first porous film having a porous, chemically etched surface upon which said first electrode is formed;

a first electrode of a porous layer of metal having a catalytic action, said first electrode being formed on said first porous film such that component grains of said first electrode penetrate into said first porous film;

a second porous film formed on said first electrode for protecting said first electrode from the gas under test;

a second electrode formed on an opposite surface of said oxygen concentration sensing element; wherein said automotive oxygen sensor demonstrates a response time of (1) about 100 milliseconds when the air-fuel mixture supplied to said engine changes from rich to lean from 0.9 to 1.0 and the output voltage of said sensor changes from 0.6 volts to 0.3 volts, and (2) about 50 milliseconds when the air-fuel mixture supplied to said engine changes from lean to rich from 1.1 to 0.9 and the output voltage of said sensor changes from 0.3 to 0.6 volts.

* * * * *